United States Patent [19]

Hoppe et al.

[11] 4,296,095

[45] Oct. 20, 1981

[54] DENTAL AND MOUTH CARE PREPARATIONS

[75] Inventors: Udo Hoppe, Hamburg; Gerhard Sauermann, Wiemersdorf; Julius Curts, Hamburg, all of Fed. Rep. of Germany; Per-Olof Glantz, Lund, Sweden; Bo Krasse, Askim, Sweden; Kåre Larsson, Hovas, Sweden; Börje Norén, Upsala, Sweden; Göran Odham, Södra Sandby, Sweden; Jan Olsson, Hovas, Sweden

[73] Assignee: Beiersdorf Aktiengesellschaft, Hamburg, Fed. Rep. of Germany

[21] Appl. No.: 944,195

[22] Filed: Sep. 20, 1978

[30] Foreign Application Priority Data

Sep. 21, 1977 [DE] Fed. Rep. of Germany ....... 2742411

[51] Int. Cl.³ .................. C07C 101/24; A61K 7/22

[52] U.S. Cl. .................. 424/52; 560/169; 424/54

[58] Field of Search .................. 560/169; 424/52, 54

[56] References Cited

U.S. PATENT DOCUMENTS 3,433,779  3/1969  Vogler .................. 560/169

*Primary Examiner*—Natalie Trousof
*Assistant Examiner*—Michael Shippen
*Attorney, Agent, or Firm*—Bierman & Bierman

[57] ABSTRACT

A composition is disclosed which is useful in preventing dental plaque and tartar from forming on the teeth. The composition includes compounds which are esters or their mono or double salts derived from lysine in combination with straight chain or branched, saturated or unsaturated, monovalent aliphatic alcohols having 4 to 20 carbon atoms.

10 Claims, No Drawings

DENTAL AND MOUTH CARE PREPARATIONS

The invention relates to dental care agents, such as toothpastes, tooth powders, tooth tablets, gel-type tooth cleaning preparations or the like, and mouth care agents, such as mouth washes, mouth sprays, chewable tablets and chewing gum which, due to an active substance contained therein, prevents the formation of dental plaque and tartar which can lead to caries and periodontosis.

BACKGROUND OF THE INVENTION

It is known that absorption of bacteria by dentin results in the formation of plaque on tooth surfaces. The buildup of plaque is the cause of caries and periodontosis. Systematic studies by Muhlemann, et al have shown that cations with a multiple positive charge exert a caries-protective effect. In particular, hydrophobic cations in such compounds as alkyl ammonium fluorides, demonstrate that the caries-protective effect must be attributed mainly to the cation rather than the fluoride anion.

Quaternary, long-chain compounds of this type possess considerable anti-microbial activity, as does sodium-palmitoyl-L-lysine-L-lysine ethyl ester dihydrochloride and sodium-palmitoyl-L-lysine-L-lysine amide dihydrochloride (e.g. German Pat. No. 1 154 236). Therefore, when used regularly, they can influence the composition of the oral microbial flora and alter it in an undesirable manner. Moreover, the toxicity of long-chain quaternary compounds is considerable and is a factor which cannot be ignored.

It is an object of the present invention to overcome the disadvantages associated with known caries-prophylactic compounds and to develop non-toxic substances which, in addition to inhibiting caries and periodontosis development, have, at the same time, a very low anti-microbial activity.

It is an additional object of this invention to provide suitable dental and mouth care preparations containing these substances.

It has now been found that esters, as well as their mono and double salts, of a certain diamino-monocarboxylic acid; namely, lysine ($\alpha,\beta$-diamino-n-caproic acid), exhibit a very good bacterial adhesion inhibiting effect combined with very low bacteriostatic activity and toxicity. This makes their use in dental and mouth care preparations especially valuable.

The use of such preparations in the mouth results in a decrease in the number of colony-forming units of bacterial oral flora on tooth surfaces. This effect is associated with a decrease in the formation of dental plaque which in turn results in a similar decreased tendency towards caries and periodontosis. Prevention of the formation of plaque and tartar is presently regarded as the most important means of preventing the spread of dental caries and periodontous diseases.

SUMMARY OF THE INVENTION

The subject matter of the present invention is thus a dental and/or mouth care preparation characterized as containing therein an active substance broadly defined as esters or their mono or double salts of lysine.

More specifically, the present preparation contains a compound of the formula

$NH_2CH_2(CH_2)_3CH(NH_2)COOR \cdot X_n$ wherein R is selected from the group consisting of straight or branched chain alkyl, alkenyl, and acyl having 4 to 20 carbon atoms, X is a group which renders said compound a salt and n has a value of 0, 1, or 2.

Members for R include n-butyl, isobutyl, 2-ethylhexyl, decyl, arachidyl, oleyl, and in particular myristyl, palmityl, cetyl, and stearyl. A preferred form of the invention arises when the carbon content of R is limited to 14 to 18 carbon atoms.

Because of their better stability and more reliable solubility, the dental and mouth care preparations of the present invention preferably incorporate therein the mono and double salts of the lysine esters. More specifically, the hydrochlorides, hydrofluorides, gluconates, monoacetates, phosphates and sulfates are preferred. An especially good bacteria adhesion inhibiting effect along with low bacteriostatic activity can be achieved by the use of the dihydrochlorides of lysine, palmityl ester.

The production of the lysine esters and their salts used according to the invention is achieved in a known manner. For example, lysine decyl ester dihydrochloride can be produced as follows.

1.0 g L-lysine monohydrochloride was added to 100 ml of a solution of hydrogen chloride in methanol (1.25 M) and the resulting mixture was heated for one hour at 80° C. After standing at room temperature for several hours, the solution was concentrated in a vacuum until dry. The yield of lysine methyl ester dihydrochloride was 1.5 g. 50 ml of decyl alcohol (n-decanol) were added to the 1.5 g of dihydrochloride and the mixture was then heated for 3 hours at 105° C. while bubbling through dry hydrogen chloride. Then, the reaction mixture was cooled and left standing at room temperature for several hours. The resulting crystals were filtered out and washed on the filter with a small quantity of dry ether. The yield of lysine decyl ester dihydrochloride was 1.1 g (43.7% of the theoretical). Mass spectrum and C, H, N analysis confirmed the structure and purity of the compound.

Furthermore, one of the most preferred compounds: lysine palmityl ester dihydrochloride can be prepared in the following manner:

A mixture of 18.2 g (0.1 mole) 1-lysine monohydrochloride, 45.6 g (0.24 moles) p-toluenesulphonic acid, 27 g (1.1 moles) palmityl alcohol (hexadecanol-1) and 250 ml toluene was heated under stirring until water begins to distil and the reaction temperature was then maintained at 130°-140° C. for approximately six hours (till the separation of water was finished). Subsequently the toluene was distilled off in vacuo. The waxy product, the di-p-toluenesulphonate salt of 2,6-diamino-n-hexadecyl caproate, was recrystallized from a mixture of methanol and diethyl ether.

A solution of 51.7 grams of this product in 106 ml methanol was adsorbed on a column of 500 ml of a strongly basic styrenedivinylbenzene anion-exchange resin (Dower 1-X 8) which has previously been activated on the hydroxyl cycle with aqueous ammonia, washed to neutrality, and had its water displaced with methanol. The product was eluted from the column with methanol. The free base ester was not isolated but converted to the dihydrochloride of lysine palmityl ester by addition of anhydrous HCl and the dihydrochloride recovered by precipitation with diethyl ether. Yield: 8.8 g.

The testing of the compound for reduced bacteria adhesion (bacteria adhesion inhibiting effect) was carried out in a manner analogous to the method described by J. Olsson and B. Krasse (Scand. J. Dent. Res. 84 (1976), p 20–28).

More specifically, the compounds are dissolved in a potassium phosphate buffer solution containing common salt ($K_2HPO_4/KH_2PO_4$ 0.05 mole; NaCl 0.154 mole) of pH 7.3 (PBS(=phosphate buffered saline)) or in ethanol. Whale dentin pieces having a length of 8 mm and a thickness of 1.5 mm were immersed into the solution for 15 minutes. Control samples were immersed for the same period of time into PBS or ethanol absent the active ingredient.

The incubation medium was prepared by making a solution containing 2% of the active substance in PBS. If the solubility is such that a 2% solution cannot be achieved, a saturated solution is sufficient. This solution was then mixed with a paraffin-stimulated saliva mixture having a volume ratio of 1:1.

The treated whale dentin pieces were placed in the above-described medium for 40 minutes at 37° C. Thereafter, each piece was shaken in a 1 ml nutrient solution present in each of three successive plastic tubes and then pressed down on the same side into MS Agar (Mitis Salivarious Agar). 0.1 ml portions of each of the last tube, the combined content of all three tubes, and the incubation medium, were each uniformly diluted with PBS. The resulting mixtures were spread on MS agar and incubated aerobically for 48 hours.

The relative degree of bacterial absorption was determined by the number of colony-forming microorganisms that could be removed from the test pieces, taking into account the units removed from the control pieces.

The results are shown in Table I.

TABLE II

| Whale dentin chips treated with: | Relative number of colony-forming units | |
|---|---|---|
| | Combined wash soln. (1-3) | Last wash soln. (3) |
| Control | 100 | 100 |
| 1% Lysine-n-butylester dihydrochloride | 47 | 70 |
| 1% Lysine decyl ester dihydrochloride | 29 | 54 |
| 1% Lysine palmityl ester dihydrochloride | 20 | 20 |
| 1% Lysine-n-butyl ester | 59 | 40 |

It is evident from the values shown in Table I for the last wash solution that the use of lysine-n-butylester dihydrochloride reduces the number of colony-forming bacteria units by 30% and by 46% when lysine decyl ester dihydrochloride is used. Additionally, an 80% reduction of the bacteria units is observed when lysine palmityl ester dihydrochloride is utilized. This is clear evidence indicating an increasing reduction of the number of colony-forming bacteria units as the number of carbon atoms in the hydrophobic component of the lysine ester increases. Further, additional tests have shown that identical values are obtained when substituting the dihydrofluorides of the respective lysine esters for the dihydrochlorides.

The antimicrobial activity was determined by the method of Ericsson and Sherris (Acta Pathol. Microbiol. Scand. Sect. B, Suppl. 217). Blood agar plates were preinoculated for 30 minutes with *Streptococcus mutans* Ing. Britt, *Streptococcus sanguis*, Strain 804, or *Streptococcus salivarius*, Strain ATCC 8618. Round filters were impregnated with 10 ml of 0.2% chlorohexidine or 1% test solution and then dried. Then a chlorohexidine-impregnated chip treated with the test substance was placed on a plate and incubated for 18 hours at 37° C. The resulting inhibition zones were evaluated as a measure of the antimicrobial activity.

The test of antimicrobial activity conducted in the manner described showed that lysine esters of a chain length of 4 carbons and 10 carbons showed no bacteriostatic activity at all while the 16 carbon ester showed only a slightly activity.

A summary of these results clearly demonstrates that the lysine esters used according to the present invention in dental and/or mouth care preparations exhibit a very good bacteria adhesion inhibiting action coupled with only a slight bacteriostatic activity. The toxicity of the esters is negligibly low in comparison with quaternary amines.

The dental and/or mouth care preparations of the present invention may contain the active substance in dissolved or partially dissolved form or in the form of a suspension depending on the solubility and dosage of the selected lysine ester compound. Also, lysine esters or their salts may be present in the dental and mouth care preparations according to the invention encapsulated in the form of micro-capsules. These capsules can be used, for example, when brushing the teeth since they are destroyed by the pressure exerted by the brush thereby releasing the active substance. The wall material of the micro-capsules, produced by known methods of coacervation, may consist of a suitable hydrophobic or hydrophilic polymer material, depending on the type of preparation.

The compounds are generally incorporated into the dental and/or mouth care preparation in an amount between about 0.1 and 20 weight % based on the total weight of the preparation. Preferably, the amount of compound in the preparation is between about 1 and 5 weight %.

The compounds according to the present invention may be present for example in the form of a toothpaste which is produced in a known manner and contains the usual cleaning or polishing, binding, thickening and moisture-retaining agents.

Such toothpaste should contain 0.1 to 10 weight % and preferably 1 weight % based on the total weight of the sum of all ingredients of the paste of lysine ester or salt in order to obtain the effect of preventing dental plaque and tartar formation on the teeth in using the common quantity of toothpaste (the formation of at least a monomolecular layer of the lysine compound on the teeth is necessary to bring this effect).

Suitable polishing agents are, for example, aluminum oxyhydrate, calcium carbonate, calcium pyrophosphate and tricalcium phosphate. Useful as a binder or a gel forming agent, tragacanth is especially desirable. This agent and other known swelling agents of plant or synthetic origin may also serve as a basis for the production of a dental care agent in the form of a more or less transparent gel. Suitable moisture-retaining agents are for example, glycerol, mannitol and sorbitol as well as low aliphatic diols. In addition, such preparations normally contain surface-active substances, for example, polyoxyethylene sorbitane monooleate or other nonionogenic surface-active compounds. Preservatives, such as p-hydroxybenzoic acid ester, flavors, such as saccharin, sodium saccharin and cyclamates, and aromatics, such as peppermint oil, spearmint oil or anise oil are also routinely employed.

The dental care preparation according to the invention may also be in the form of a tooth powder or tooth tablet. Tooth powders are intimate mixtures of the active substances with finely divided cleaning or polishing agents with the addition of flavor correctives and aromatics and possibly surface-active substances. Tablet type preparations (tooth tablets) contain the active substances in suitable vehicles which are compacted to tablets under pressure using binders in powder form.

In order to increase their caries prophylactic effect, the dental care preparation according to the present invention may additionally contain small proportions of fluorine compounds such as sodium fluoride, potassium fluoride or ammonium fluoride.

Mouth care preparations according to the invention may be in the form of mouth washes, mouth sprays, chewable tablets or chewing gum. Mouth washes and mouth sprays are solutions of the active substances admixed with aromatics. As a general rule, solutions in water and alcohol, optionally containing small quantities of a wetting agent (surface-active substance), are filled into suitable containers in the usual quantity ratio, with or without the addition of a prepellant. Chewing gums are produced by mixing a heated chewing gum base (preferably chicle gum) with an aqueous sugar syrup (generally corn syrup or glucose), the active substance, dry sugar (cane sugar or dextrose) and aromatics. Then, the mixture is rolled out after intensive mixing, shaped into sheets and cut into strips.

Examples of the ingredients and their corresponding proportions of the preparations described above are explained more specifically with reference to the following table. These examples are for illustrative purposes only and are not meant to limit or in any way redefine the invention as described in the claims appended hereto.

TABLE II

| | Wt. % |
|---|---|
| Example 1—Toothpaste | |
| Lysine palmityl ester dihydrochloride | 1.0 |
| Aluminum oxyhydrate | 55.0 |
| Glycerol | 20.0 |
| Tragacanth | 1.0 |
| Polyoxyethylene sorbitane mono-oleate ("Tween 80") | 1.0 |
| Sodium saccharin | 0.2 |
| Aroma (peppermint oil) | 1.0 |
| Water | 20.8 |
| Example 2—Mouth wash | |
| Lysine palmityl ester dihydrochloride | 1.0 |
| Sorbitol, 70% | 5.0 |
| Reaction product of 1 mole hydr. castor oil with about 40 moles ethylene oxide ("Cremophor RH 40", BASF) | 2.0 |
| Aromatics and flavors | 1.0 |
| Ethanol, 95% | 30.0 |
| Water | 61.0 |
| Example 3—Chewing gum | |
| Chicle gum | 20.6 |
| Cane sugar | 40.0 |
| Dextrose | 22.0 |
| Corn syrup, 43° Be | 15.7 |
| Glycerol | 0.8 |
| Peppermint oil | 0.7 |

TABLE II-continued

| | Wt. % |
|---|---|
| Lysine stearyl ester dihydrofluoride | 0.2 |

What we claim is

1. A method for preventing the formation of dental plaque and tartar on teeth comprising applying to said teeth an effective amount of a composition comprising from 0.1 to 20% by weight, based on the total weight of the composition, of a compound of the formula $$H_2N.CH_2(CH_2)_3.CH(NH_2).COOR.X_n$$

wherein R is selected from the group consisting of straight chain alkyl, branched chain alkyl and alkenyl all having 14 to 18 carbon atoms, X is a group which renders said compound a salt and n has a value of 0, 1 or 2, and a carrier suitable for application to said teeth, and the inside of the mouth.

2. A method according to claim 1 wherein said composition contains between about 1 and 5% by weight, based on the total weight of the composition, of said compound.

3. A method according to claim 1 wherein R is selected from the group consisting of myristyl, palmityl, stearyl, and oleyl.

4. A method according to claim 1 wherein X is selected from the group consisting of hydrochloride, hydrofluoride, gluconate, monoacetate, phosphate and sulfate, and n is 1 or 2.

5. A method according to claim 1 wherein said compound is lysine palmityl ester dihydrochloride.

6. A method according to claim 1 wherein said carrier is selected from the group consisting of toothpaste, tooth powders, tooth tablets, gel-type cleaning preparation, mouth washes, mouth sprays, chewable tablets, and chewing gum.

7. A method according to claim 6 wherein said toothpaste, tooth powder or tooth tablet further contains a fluoride compound.

8. A method according to claim 1 wherein said effective amount comprises an amount of said composition sufficient to inhibit the adhesion of the microorganisms that cause the formation of said dental plaque and said tartar.

9. A method according to claim 1 wherein at least a monomolecular layer of said composition is formed on said teeth.

10. A method for preventing the adhesion to teeth of the microorganisms that cause dental plaque and tartar to form thereon comprising applying to said teeth an effective amount of a composition comprising from 0.1 to 20% by weight, based on the total weight of the composition, of a compound of the formula $$H_2N.CH_2.(CH_2)_3.CH(NH_2).COOR.X_n$$

wherein R is selected from the group consisting of straight chain alkyl, branched chain alkyl and alkenyl all having 14 to 18 carbon atoms, X is a group which renders said compound a salt and n has a value of 0, 1 or 2, and a carrier suitable for application to said teeth, and the inside of the mouth.

* * * * *